(12) United States Patent
Jiang et al.

(10) Patent No.: US 12,100,820 B2
(45) Date of Patent: Sep. 24, 2024

(54) INTEGRATED BATTERY USING AIRFLOW SENSOR FOR CONTROL

(71) Applicant: SHENZHEN KINGFISH ELECTRONICS TECHNOLOGY CO., LTD, Shenzhen (CN)

(72) Inventors: Xingang Jiang, Shenzhen (CN); Debao Xu, Xinyi (CN)

(73) Assignee: SHENZHEN KINGFISH ELECTRONICS TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/542,616

(22) Filed: Dec. 16, 2023

(65) Prior Publication Data

US 2024/0120561 A1 Apr. 11, 2024

(30) Foreign Application Priority Data

Jan. 4, 2023 (CN) .......................... 202310005244.8
Jan. 4, 2023 (CN) .......................... 202320007324.2

(51) Int. Cl.
*H01M 10/48* (2006.01)
*A61M 15/00* (2006.01)
*H01M 10/42* (2006.01)
*H01M 50/186* (2021.01)
*H01M 50/342* (2021.01)

(52) U.S. Cl.
CPC ....... *H01M 10/48* (2013.01); *H01M 10/4257* (2013.01); *H01M 50/186* (2021.01); *H01M 50/342* (2021.01); *A61M 15/0013* (2014.02); *A61M 2205/3334* (2013.01); *A61M 2205/8206* (2013.01)

(58) Field of Classification Search
None
See application file for complete search history.

(56) References Cited

U.S. PATENT DOCUMENTS 10,381,849 B2 * 8/2019 Wing .................... A61M 16/16
2004/0185334 A1 9/2004 Iwamoto
(Continued)

FOREIGN PATENT DOCUMENTS

CA 3047985 A1 * 12/2019 ............. A24F 40/10
CN 203467669 U * 3/2014
(Continued)

OTHER PUBLICATIONS

CN-213307437-U English machine translation (Year: 2021).*
CN-216116184-U English machine translation (Year: 2022).*
CN-215133306-U English machine translation (Year: 2021).*

*Primary Examiner* — Scott J. Chmielecki
(74) *Attorney, Agent, or Firm* — Hemisphere Law, PLLC; Zhigang Ma (57) ABSTRACT

An integrated battery using an airflow sensor for control comprises an outer casing, a cell and a PCBA. The cell and the PCBA are both arranged in the outer casing, and the PCBA is electrically connected with the cell. The PCBA is provided with a positive plate, a negative plate and an airflow sensor. The outer casing is provided with an air inlet. The airflow sensor is arranged on the battery to control discharge of the cell, such that the battery can be used together with some atomizers to realize instant atomization when users inhale, and the waste of atomizing liquid is avoided.

8 Claims, 13 Drawing Sheets

(56) References Cited

U.S. PATENT DOCUMENTS

2008/0238369 A1   10/2008  Cintra et al.
2012/0040221 A1    2/2012  Stoughton et al.
2016/0183592 A1*  6/2016  Liu ........................ A24F 40/50
                                                     131/329

FOREIGN PATENT DOCUMENTS

| | | | |
|---|---|---|---|
| CN | 204015118 U | * | 12/2014 |
| CN | 206079037 U | * | 4/2017 |
| CN | 213307437 U | * | 6/2021 |
| CN | 113144398 A | * | 7/2021 |
| CN | 215133306 U | * | 12/2021 |
| CN | 216116184 U | * | 3/2022 |
| CN | 216931884 U | * | 7/2022 |
| DE | 102021107540 A1 | * | 2/2022 ......... H02J 7/00036 |

* cited by examiner

FIG. 13

INTEGRATED BATTERY USING AIRFLOW SENSOR FOR CONTROL

BACKGROUND OF THE INVENTION

Technical Field

The invention relates to the technical field of batteries, in particular to an integrated battery using an airflow sensor for control, which is mainly applied to, but not limited to, atomizers.

Description of Related Art

In the treatment of patients, inhalation-type atomizers are used. Liquid medicine is stored in the inhalation-type atomizer; then, the atomizer atomizes the liquid medicine; and finally, the atomized liquid medicine is sprayed out via an atomization nozzle (jet nozzle) to be inhaled by patients through the mouth or nose to realize a treatment purpose.

However, existing atomizers controls power supplied by a power supply to an atomization element by means of a button switch inside the atomizers. When the atomizers are used, patients allow their mouth or nose to be close to the jet nozzle and then turn on the button switch to control the atomizers to work to generate atomizing gas to be used. The existing atomizers are difficult to operate and are generally operated by users with both hands, thus being extremely inconvenient to use especially for some special patients.

Moreover, existing batteries for atomizers merely comprise a cell and cannot intelligently control power supplied to the atomizers, so the design of circuit control has to be taken into account when the atomizers are designed, brining inconvenience to designers.

Therefore, it is necessary to figure out a new technical solution to solve the above-mentioned problems.

BRIEF SUMMARY OF THE INVENTION

To overcome the above-mentioned drawbacks and defects of the prior art, the invention provides an integrated battery using an airflow sensor for control, which controls discharge of a cell by means of an airflow sensor arranged on the battery, and thus can be used together with some atomizers to realize instant atomization when users inhale, can respond quickly and can effectively avoid a waste of electric energy of the cell and atomizing liquid;

To fulfill the above purpose, the invention adopts the following technical solution:

An integrated battery using an airflow sensor for control comprises an outer casing, a cell and a PCBA, wherein the cell and the PCBA are both arranged in the outer casing, and the PCBA is electrically connected with the cell; the PCBA is provided with an airflow sensor; the outer casing is provided with an air inlet communicated with the airflow sensor; and when the airflow sensor senses an airflow change, the PCBA controls the cell to discharge.

Preferably, the PCBA has a discharge terminal, and the discharge terminal comprises a positive plate and a negative plate arranged on the PCBA.

Preferably, a sealing gasket and an insulating support are also arranged in the outer casing, the sealing gasket is arranged on an upper side of the cell, and the PCBA is arranged on an upper side of the sealing gasket;

the PCBA is also provided with a charging port, and the charging port penetrates through the insulating support and extends out of an upper surface of the outer casing; and, an air inflow gap is reserved between the charging port and the insulating support, and the air inflow gap forms the air inlet.

Preferably, an air outlet is formed in a lower surface of the outer casing, and an air duct gap is reserved between the cell and an inner wall of the outer casing.

Preferably, the sealing gasket is provided with an air hole corresponding to the airflow sensor.

Preferably, the outer casing is made from an electrically conductive material, wherein the positive plate is electrically connected with the outer casing, and the negative plate is arranged on an upper surface of the insulating support.

Preferably, the insulating support is provided with a mounting recess for mounting the negative plate, the negative plate is mounted on the mounting recess, and an insulating ring portion is arranged between an outer edge of the negative plate and an outer edge of the insulating support.

Preferably, the airflow sensor is a MEMS microphone.

Preferably, the PCBA is integrated with a battery protection chip and a main control chip, a positive pole of the cell is connected with a first resistor and is connected to the battery protection chip through the first resistor, a power output terminal of the battery protection chip is connected with the airflow sensor, an output terminal of the airflow sensor is connected with the main control chip, and an output terminal of the main control chip is connected with an output load and an indicator light.

Compared with the prior art, the invention has remarkable advantages and beneficial effects. Specifically, as can be known from the above technical solution, the airflow sensor is arranged on the battery to control discharge of the cell, such that the battery can be used together with some atomizers to realize instant atomization when users inhale; and the integrated battery can respond quickly and can effectively avoid a waste of electric energy of the cell and atomizing liquid;

In addition, the integrated battery provided by the application has the advantage of high adaptability. The integrated battery is identical in overall shape and specification with other batteries on the market, and thus can be directly assembled together with other parts of atomizers, can be directly assembled on other products to be manufactured as a whole, and in subsequent production, can quickly respond to the demands in sales areas, thus having a broad market prospect.

To more clearly expound the structural features and effects of the invention, the invention will be described in detail below in conjunction with accompanying drawings and embodiments.

REFERENCE SIGNS

10, outer casing; 11, air outlet; 12, air duct gap; 20, cell; 30, PCBA; 31, positive plate; 32, negative plate; 321, air inflow notch; 33, airflow sensor; 34, charging port; 341, air inflow gap; 40, sealing gasket; 41, air hole; 50, insulating support; 51, mounting recess; 52, insulating ring portion.

DETAILED DESCRIPTION OF THE INVENTION

The technical solutions in embodiments of the invention will be clearly and completely described below in conjunction with accompanying drawings. Obviously, the embodiments in the following description are merely preferred ones of the invention.

It should be noted that when one element is referred to as being "fixed to" the other element, it may be directly located on the other element or there may be an element between the two elements. When one element is referred to as being "connected to" the other element, it may be directly connected to the other element or there may be an element between the two elements. Terms such as "vertical", "horizontal", "left" and "right" and similar expressions used in this specification are merely for the purpose of description, and do not indicate a unique implementation.

Unless otherwise defined, all technical and scientific terms used in this specification have the same meanings as commonly understood by those skilled in the art. All terms used in the description of the invention are merely for the purpose of describing specific implementations and are not intended to limit the invention. The term "and/or" used in the specification indicates that any one and all combinations of one or more related items listed are included.

Referring to FIG. 1-FIG. 13 which illustrate multiple embodiments of the invention. An embodiment of the invention provides an integrated battery using an airflow sensor for control, comprising an outer casing 10, a cell 20 and a printed circuit board (PCBA) 30, wherein the cell 20 and the PCBA 30 are both arranged in the outer casing 10, and the PCBA 30 is electrically connected with the cell 20; the PCBA 30 is provided with a positive plate 31, a negative plate 32 and an airflow sensor 33; and the outer casing 10 is provided with an air inlet communicated with the airflow sensor 33.

When sensing an airflow change, the airflow sensor 33 generates a trigger signal and sends the trigger signal to the PCBA 30; after receiving the trigger signal, the PCBA 30 instantly controls the cell 20 to discharge (specifically, an external load is correspondingly connected to the positive plate 31 and the negative plate 32, and the PCBA 30 controls the cell 20 to discharge through the positive plate 31 and the negative plate 32).

The integrated battery provided by the application can be applied to atomizers (for example, medicine atomizers in the medical field). When applied to an atomizer, the integrated battery provided by the invention is mounted in the atomizer and electrically connected with an atomization element in the atomizer. When users inhale with their mouth being aligned with an atomization port of the atomizer, an air pressure change (and an airflow) will be produced in the atomizer and trigger the airflow sensor 33, and then the PCBA 30 controls the cell 20 to discharge; at this moment, under the action of power supplied by the cell 20, the atomization element in the atomizer starts to work to atomize liquid medicine, and then the atomized liquid medicine flows out via the atomization port to be inhaled by users. In this way, the operating frequency of the atomizer is kept consistent with the inhalation frequency of users, and atomization is carried out regularly, thus avoiding a waste of atomizing liquid (liquid medicine); and the integrated battery allows the atomizer to atomize liquid medicine instantly when users inhale, can respond quickly and is convenient to use. In addition to medical atomizers, the integrated battery can also be applied to other atomization products, airflow detectors (for example, airflow sensors with different sensitivities can be used to test different scales of airflow; when triggered, the airflow sensor sends a correspondingly signal to the PCBA, and then the PCBA controls the cell to supply power to an alarm to give an alarm), electronic cigarettes, and other products.

Specifically, the cell 20 is preferably a lithium cell. A lower end of the outer casing 10 is provided with a limit wall, and an upper end of the outer casing 10 is provided with a first opening; a sealing gasket 40 and an insulating support 50 are arranged in the outer casing 10; and the sealing gasket 40 is arranged on an upper side of the cell 20, and the PCBA 30 is arranged on an upper side of the sealing gasket 40;

The PCBA 30 is also provided with a charging port 34, and the charging port 34 penetrates through the insulating support 50 and extends out of an upper surface of the outer casing 10. The charging port 34 is generally a type-c port. Of course, the charging port 34 may also be a Micro USB port, a Type-B port, or other charging ports.

Figure 12:
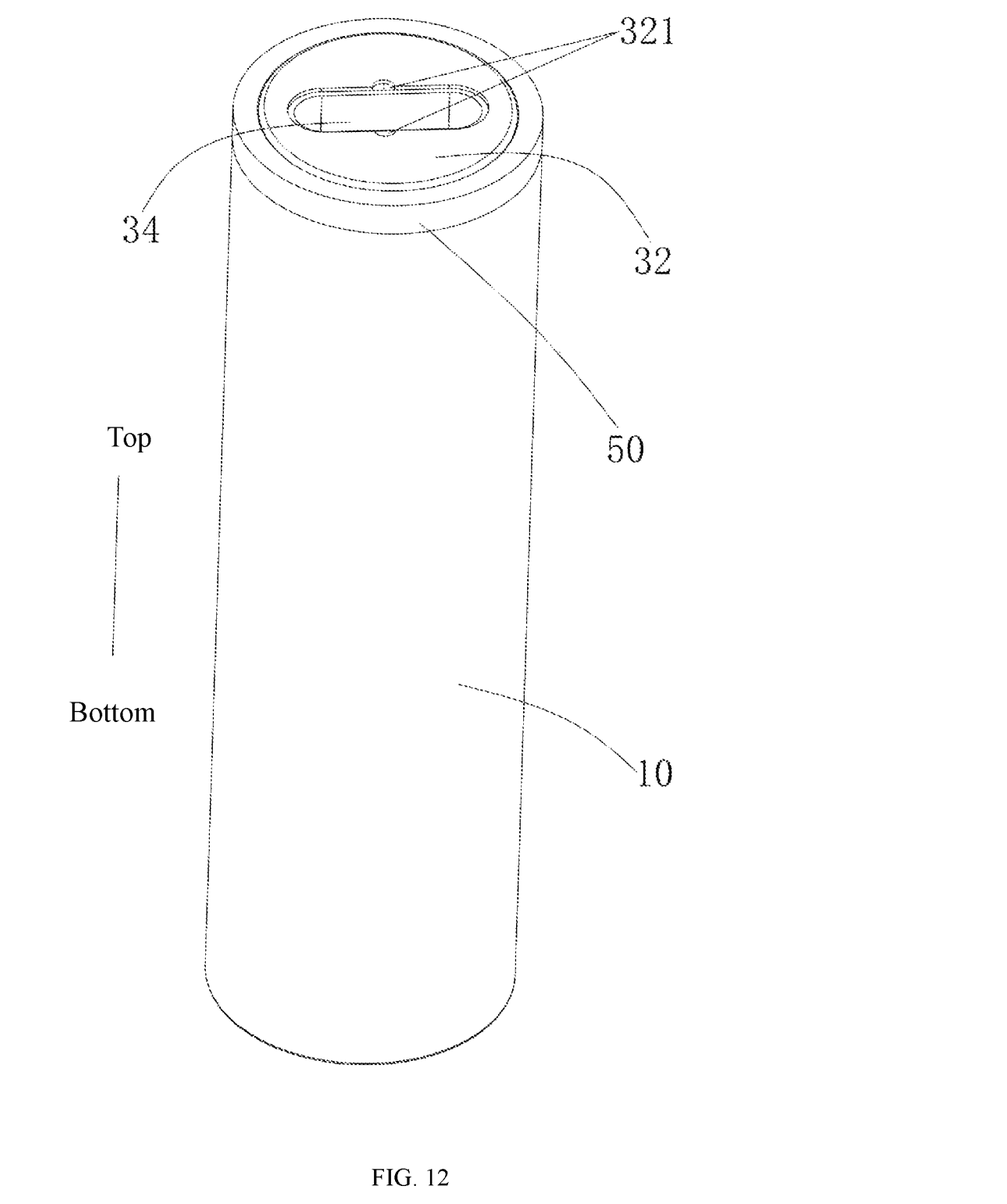
FIG. 12 is a three-dimensional view of a third embodiment of the invention.
Figure 13:
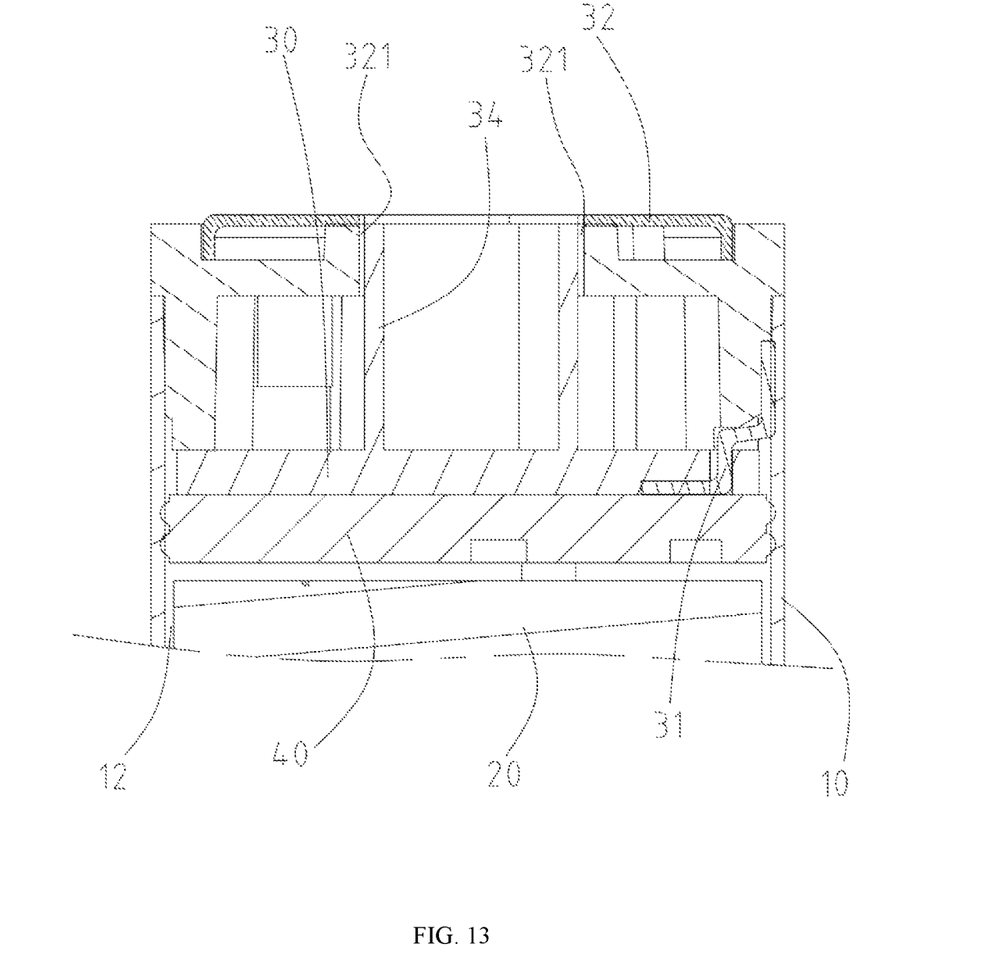
FIG. 13 is a partial sectional view of the third embodiment of the invention.

An air inflow gap 341 is reserved between the charging port 34 and the insulating support 50, and the air inflow gap 341 forms the air inlet (that is, in this embodiment, the air inlet is the air inflow gap 341; and a weld gap exists between the charging port 34 and the PCBA 30 actually, and the weld gap also forms another air inlet). Of course, as shown in FIG. 12 and FIG. 13, corresponding air inflow notches 321 may be directly formed in the negative plate 32 and the insulating support 50, and the air inflow notches 321 form the air inlets. In addition, the sealing gasket 40 is provided with an air hole 41 corresponding to the airflow sensor 33, such that an airflow entering via the air inflow gap 341 can flow out via an air outlet 11 mentioned below. When assembled, the cell 20, the sealing gasket 40, the PCBA 30, the insulating support 50 and the negative plate 32 are mounted in the outer casting 10 through the first opening of the outer casing 10. Thus, the integrated battery is easy to assemble.

Further, the air outlet 11 is formed in a lower surface of the outer casing 10, and an air duct gap 12 is reserved between the cell 20 and an inner wall of the outer casing 10. During work, an airflow enters the outer casing 10 from the outside via the air inlet (the air inflow gap 341) and flows towards the air hole 41 of the sealing gasket, and at this moment, the airflow sensor 33 arranged at the air hole 41 will be triggered; then, the airflow passes through the air hole 41, reaches the air outlet 11 along the air duct gap 12 between the cell 20 and the outer casing 10, and finally flows out of the outer casing 10.

It should be noted that in actual assembly, a minor gap is reserved between a lower surface of the PCBA 30 and an upper surface of the sealing gasket 40 and a minor gap is reserved between a circumferential surface of the PCBA 30 and the outer casing 10 (or, a notch is formed in an outer edge of the PCBA 30) to allow the airflow to pass through to trigger the airflow sensor 33. Of course, a corresponding air hole 41 may be formed in the PCBA 30 to allow the airflow to pass through to trigger the airflow sensor 33.

Further, the outer casing 10 is made from an electrically conductive material. Wherein, the positive plate 31 is electrically connected with the outer casing 10, and the negative plate 32 is arranged on an upper surface of the insulating support 50. The insulating support 50 can fix the PCBA 30 and the negative plate 32 and can also space the negative plate 32 apart from the positive plate 31 (as well as the outer casing 10). Specifically, the insulating support 50 is provided with a mounting recess 51 for mounting the negative plate 32, the negative plate 32 is mounted in the mounting recess 51, and an insulating ring portion 52 is arranged between an outer edge of the negative plate 32 and an outer edge of the insulating support 50.

Preferably, the airflow sensor 33 is a Micro-electromechanical Systems (MEMS) microphone, which has a small size, can be easily pasted on a PCB; and the airflow sensor has good water-proof and oil-proof effects and is suitable for atomizers. The operating principle of the airflow sensor is as follows: when sensing an air pressure change, the airflow sensor 33 sends a trigger signal to the PCBA 30 (a MEMS chip inside the MEMS microphone converts the air pressure change into a capacitance change, and a user operation is determined by means of an ASIC chip to output a corresponding signal). The MEMS microphone may be an MSP01-GAL3 or Mic.X-2718AM-N10 MEMS microphone, or other types of MEMS microphones.

Figure 1:
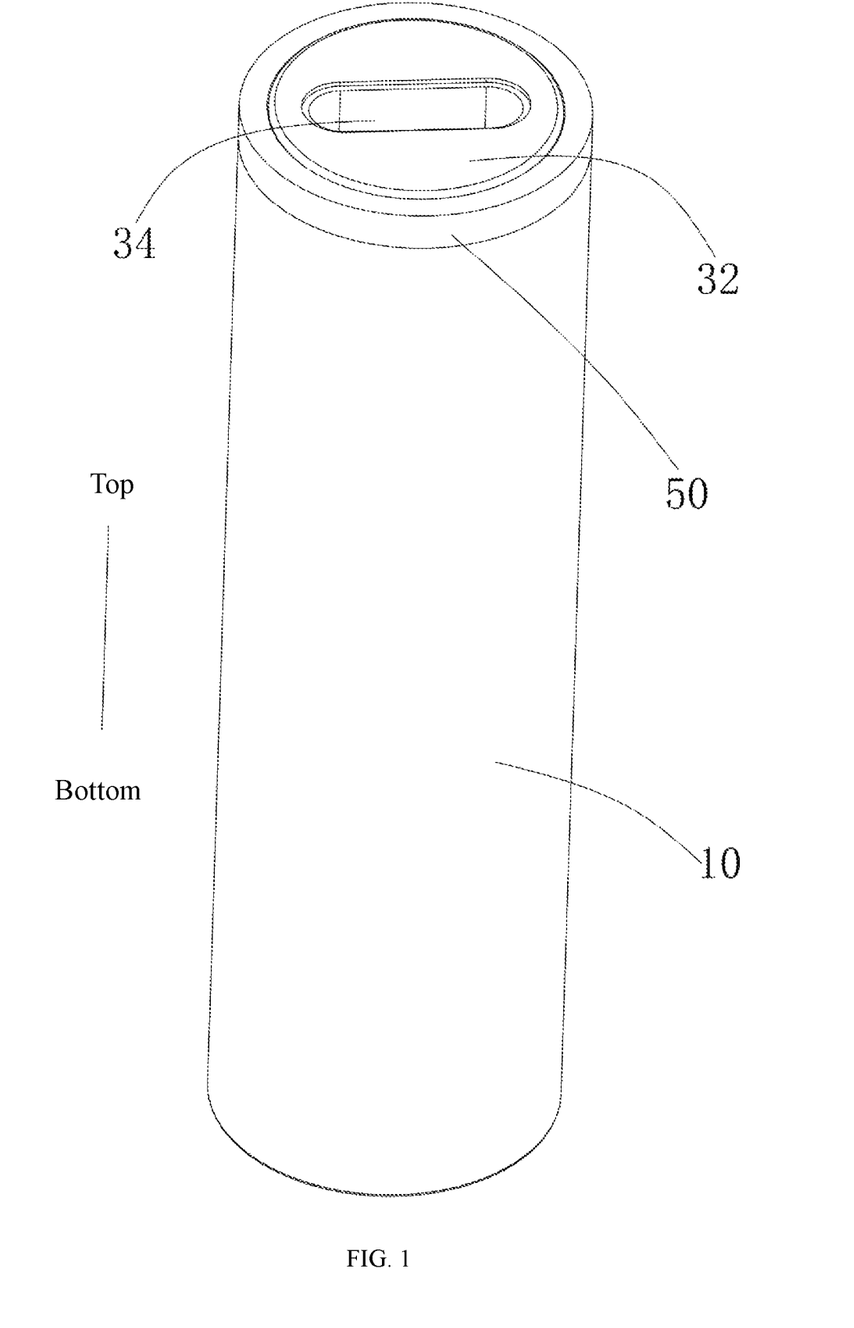
FIG. 1 is a three-dimensional view of a first embodiment of the invention.
Figure 2:
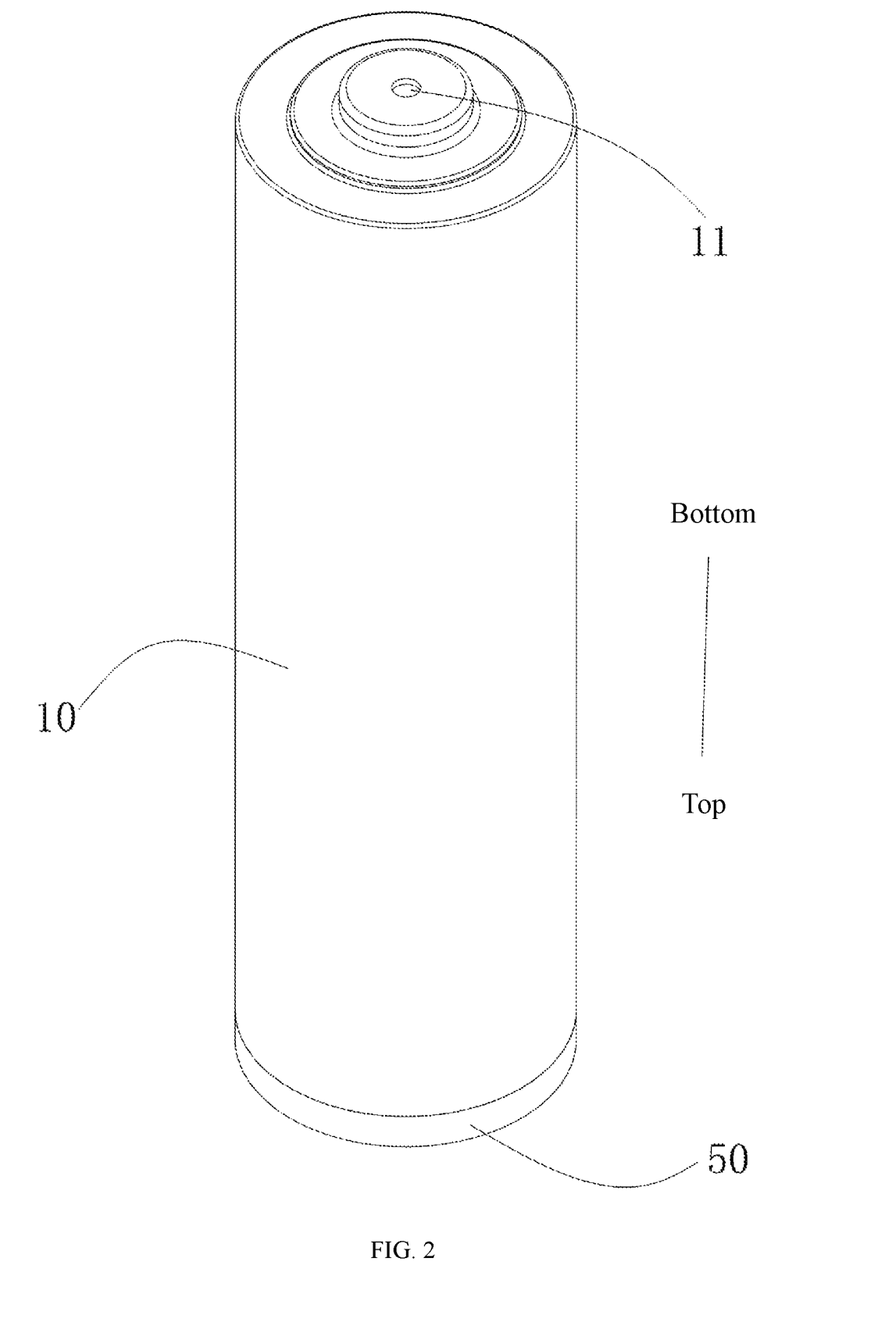
FIG. 2 is a three-dimensional view of the first embodiment of the invention, from another perspective.
Figure 3:
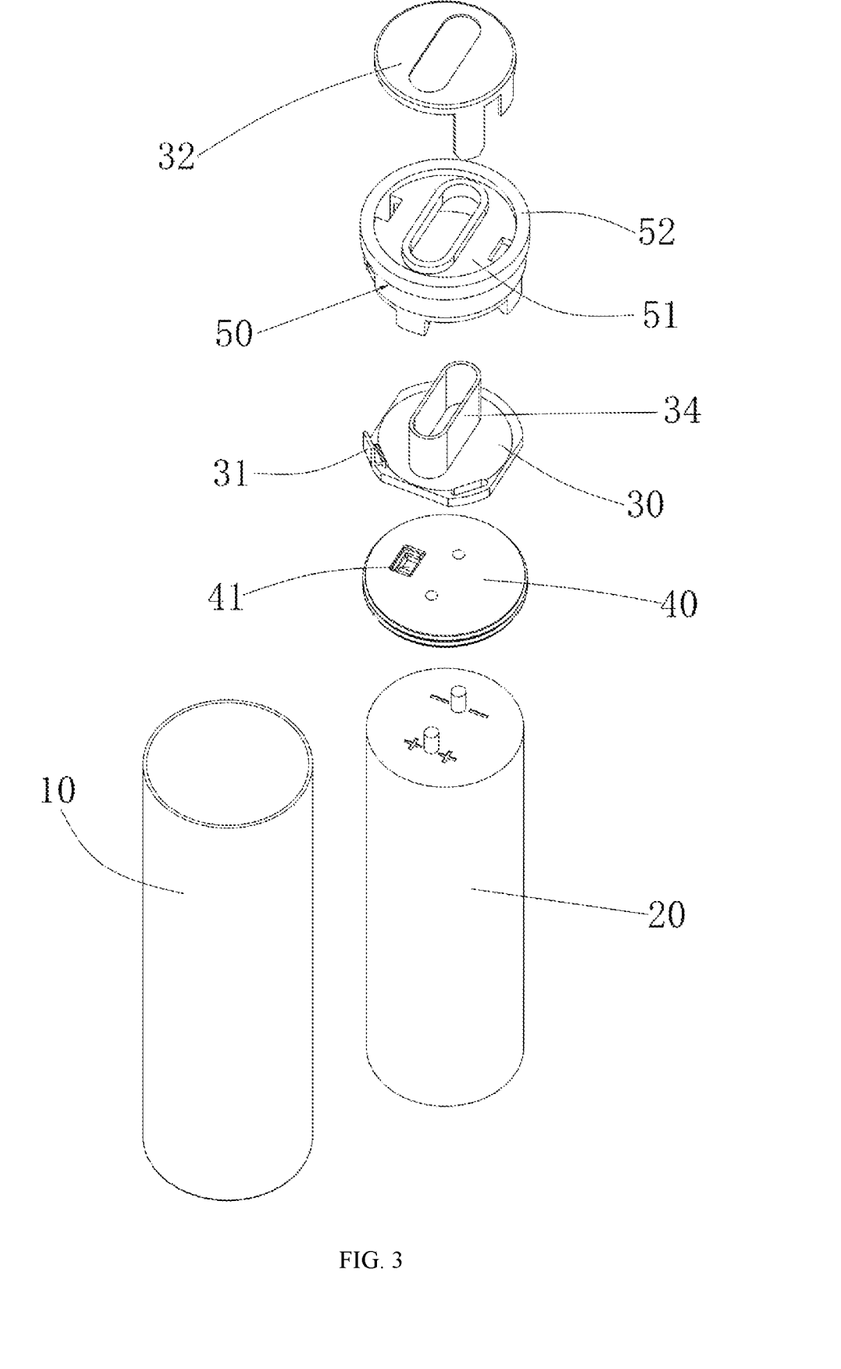
FIG. 3 is a first exploded view of the first embodiment of the invention.
Figure 4:
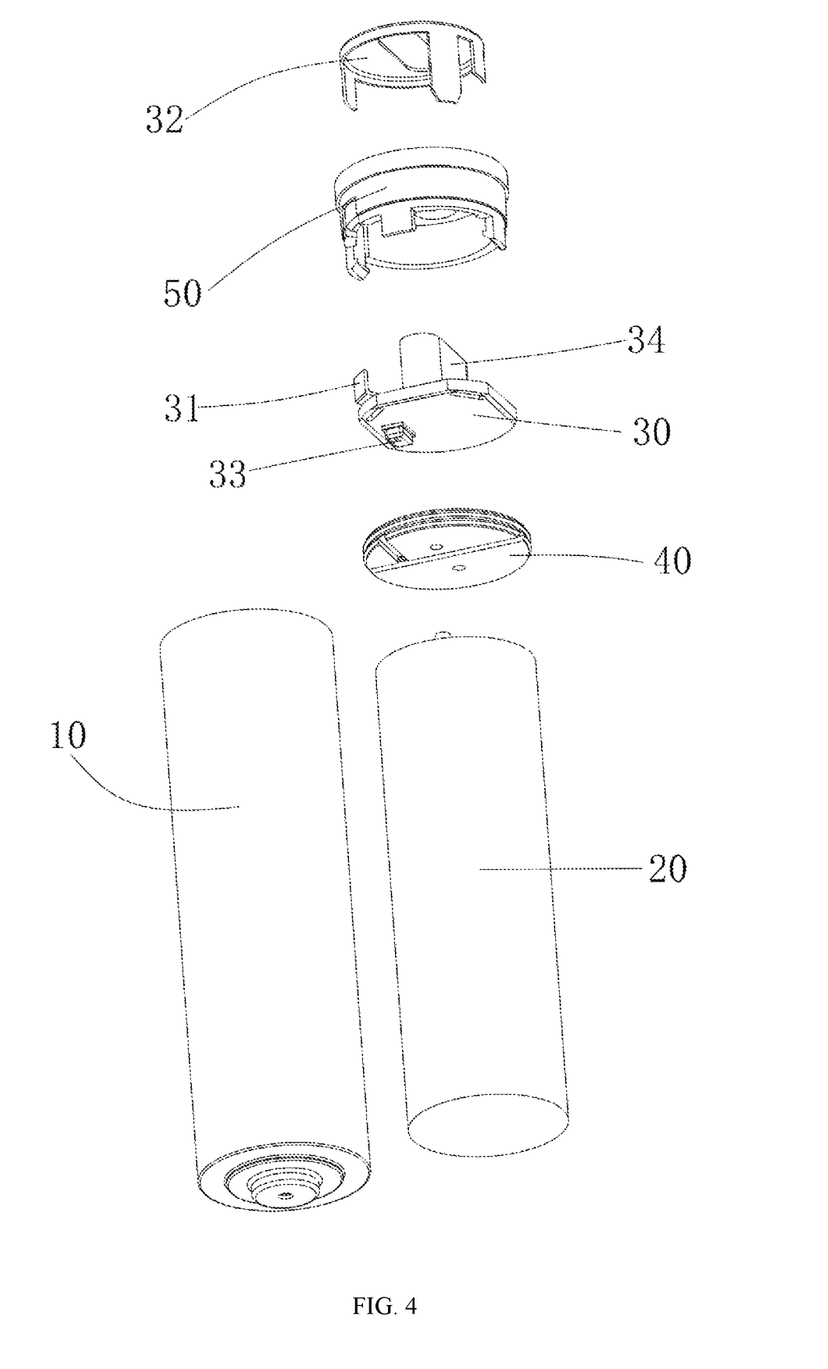
FIG. 4 is a second exploded view of the first embodiment of the invention.
Figure 5:
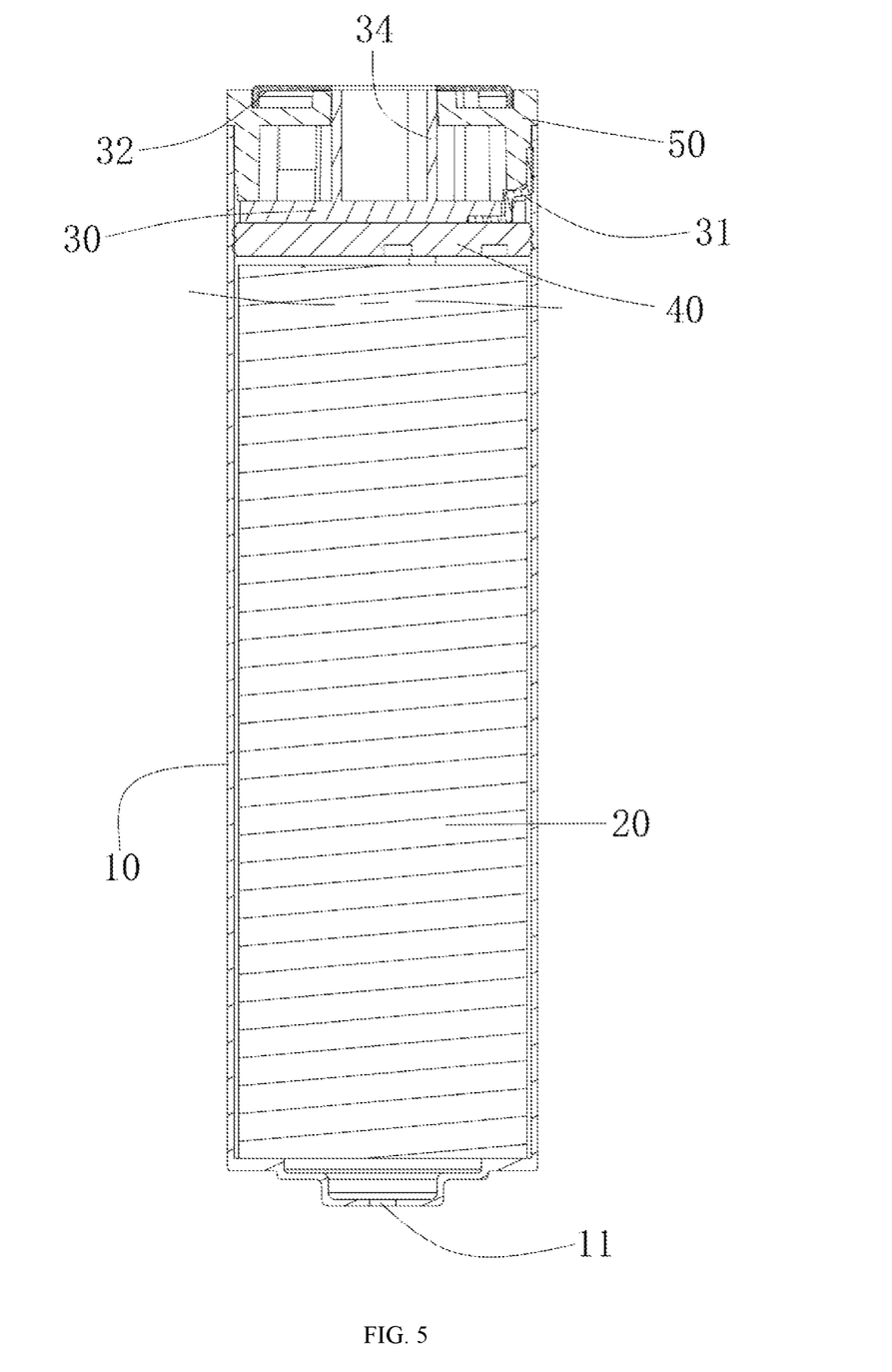
FIG. 5 is a first sectional view of the first embodiment of the invention.
Figure 6:
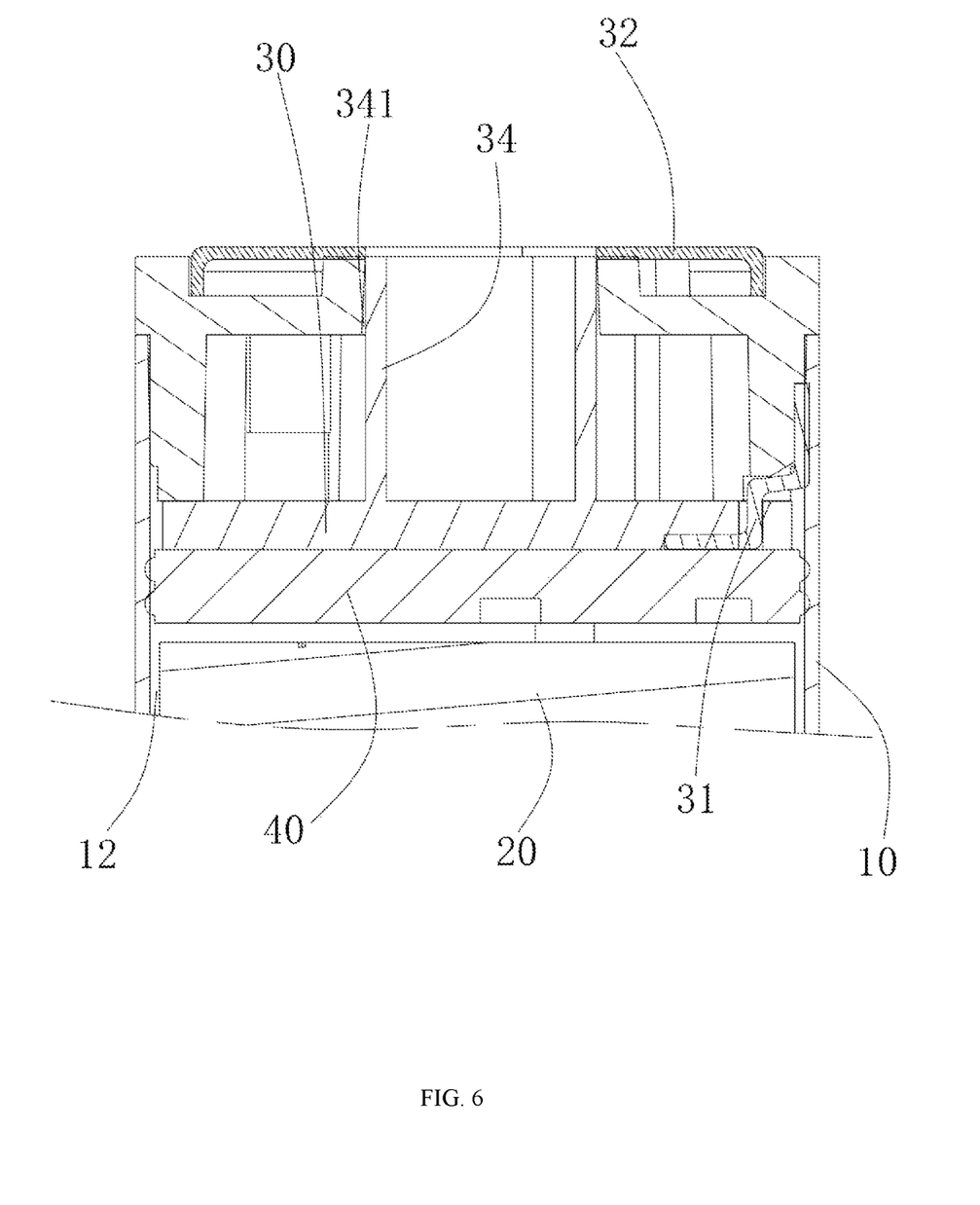
FIG. 6 is a partial enlarged view of FIG. 5.
Figure 7:
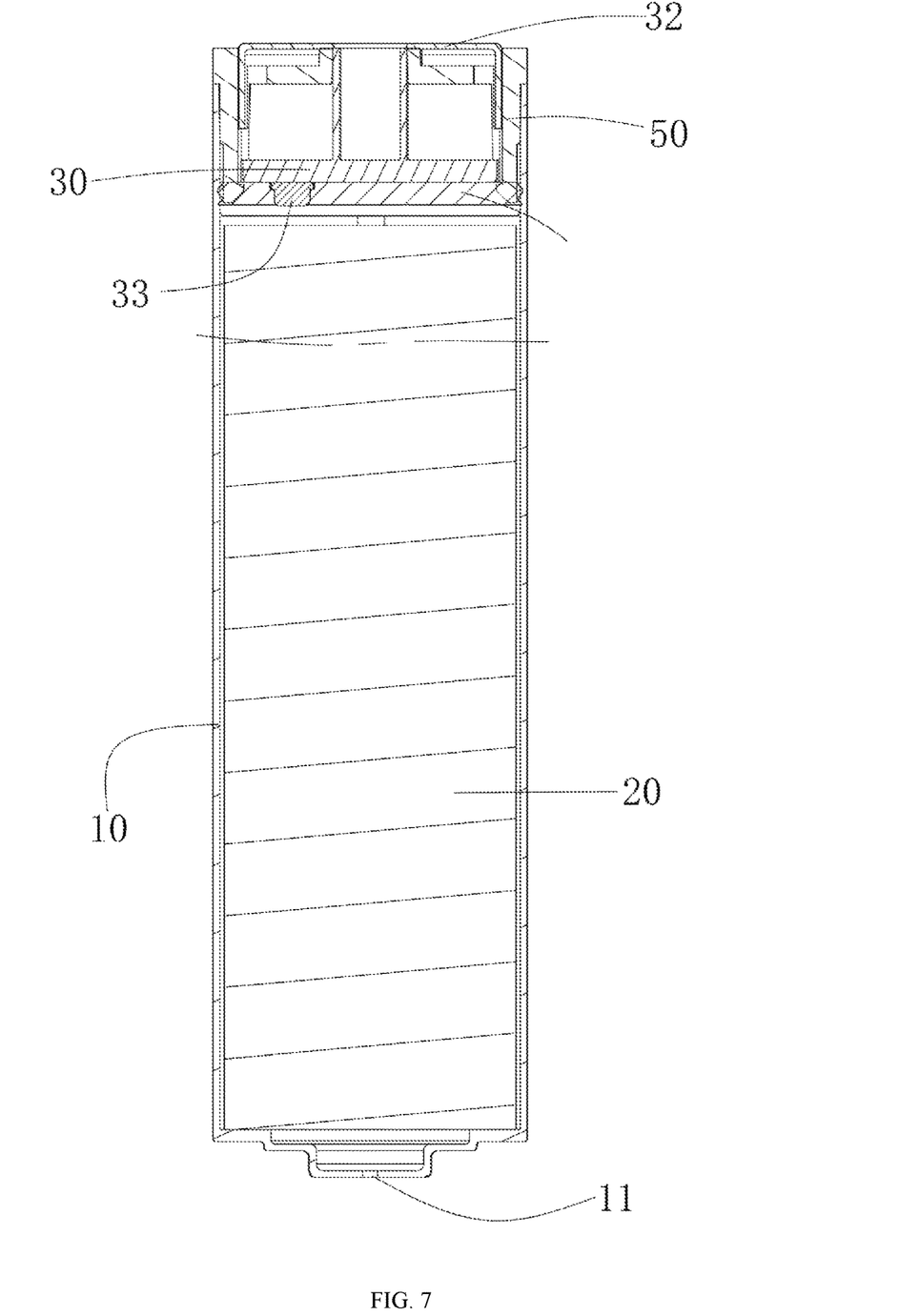
FIG. 7 is a second sectional view of the first embodiment of the invention.
Figure 8:
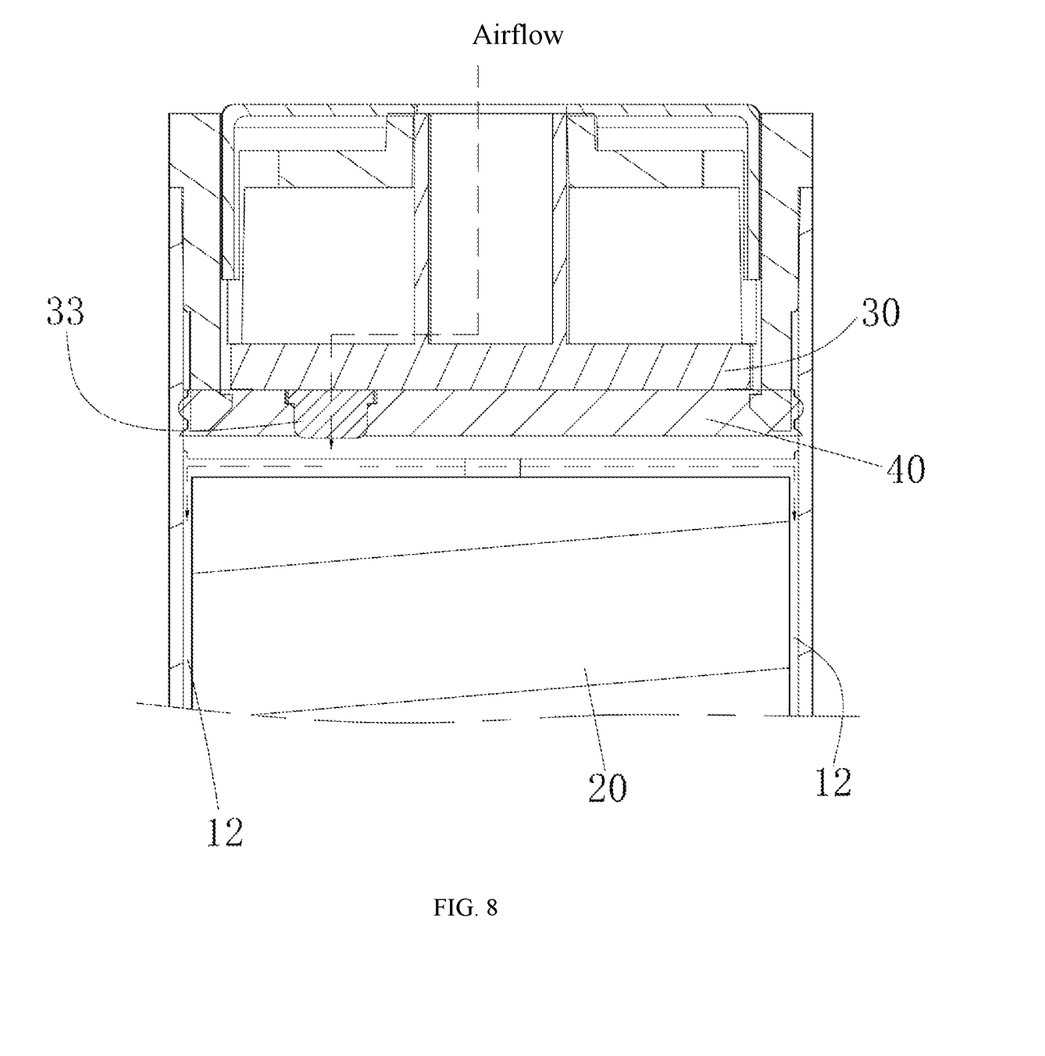
FIG. 8 is a schematic diagram of the airflow direction according to the first embodiment of the invention.
Figure 9:
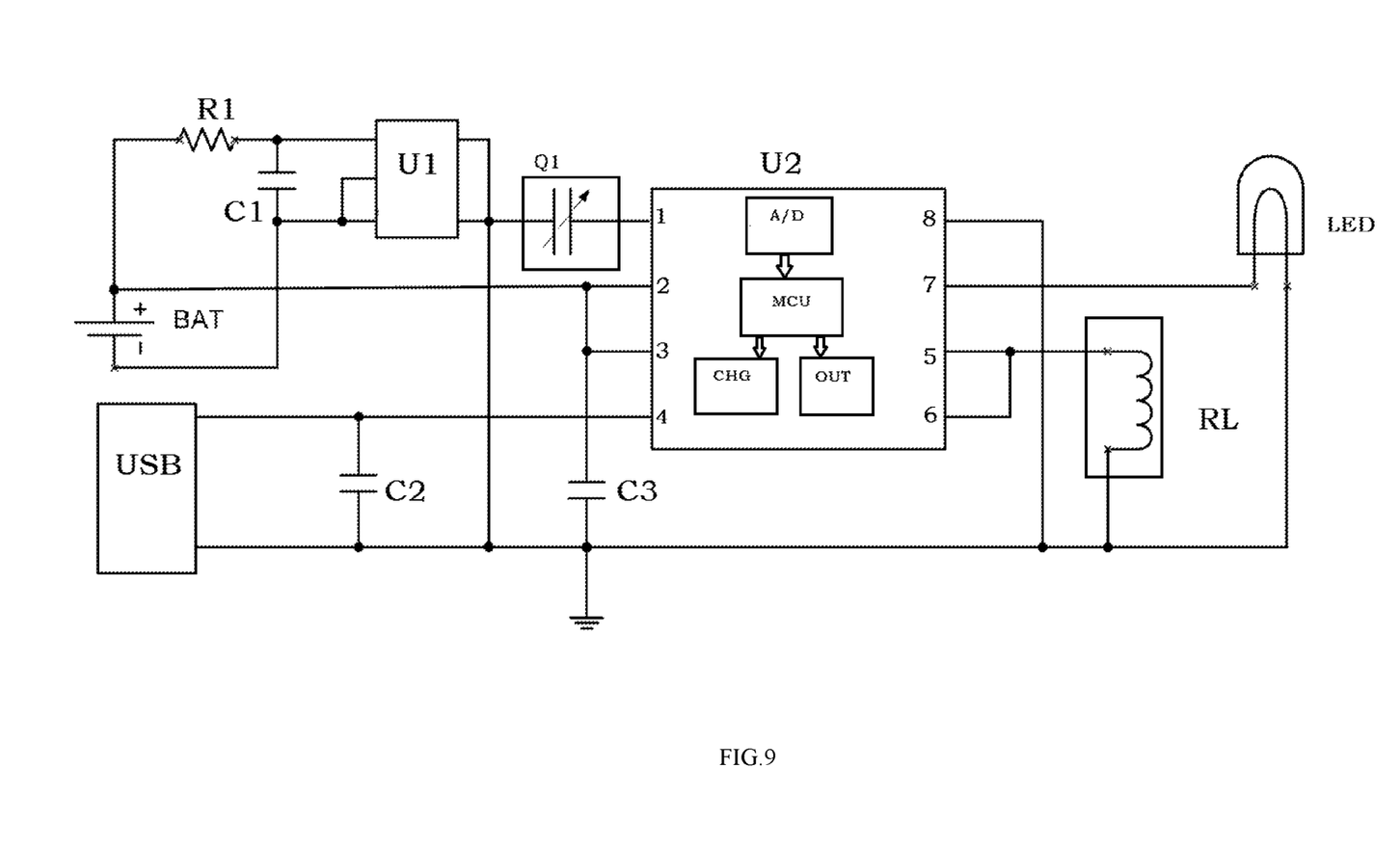
FIG. 9 is a circuit diagram of the first embodiment of the invention.

Further, referring to FIG. 9, the PCBA 30 is integrated with a battery protection chip (U1) and a main control chip (U2), a positive pole of the cell 20 is connected with a first resistor (R1) and is connected to the battery protection chip (U1) through the first resistor (R1), a power output terminal of the battery protection chip (U1) is connected with the airflow sensor 33 (Q1), an output terminal of the airflow sensor 33 (Q1) is connected to the main control chip (U2), and an output terminal of the main control chip (U2) is connected with an output load (RL) and an indictor light (LED). The detecting an airflow, the airflow sensor 33 (Q1) generates a signal and sends the signal to a 1PIN of the main control chip (U2), the main control chip (U2) converts the analog signal sent from the airflow sensor 33 (Q1) into a digital signal (the main control chip is provided with an analog-to-digital conversion module, a logic control module, a charging management module, and an output drive module), a switch of a 2PIN in the main control chip (U2) is turned on after logic control, and a stable voltage is output by means of a 5PIN of the main control chip (U2). When the airflow sensor 22 (Q1) detects no airflow, the 5PIN of the main control chip (U1) will not output a voltage. It should be noted that the battery protection chip may be XB5606 and the main control chip may be CSC909DC or BC8919B/C/D.

In this way, through the specific design of circuit control, the cell 20 is protected, and power is saved; moreover, the circuit is ingenious in design and easy to realize, and facilitates production.

Figure 10:
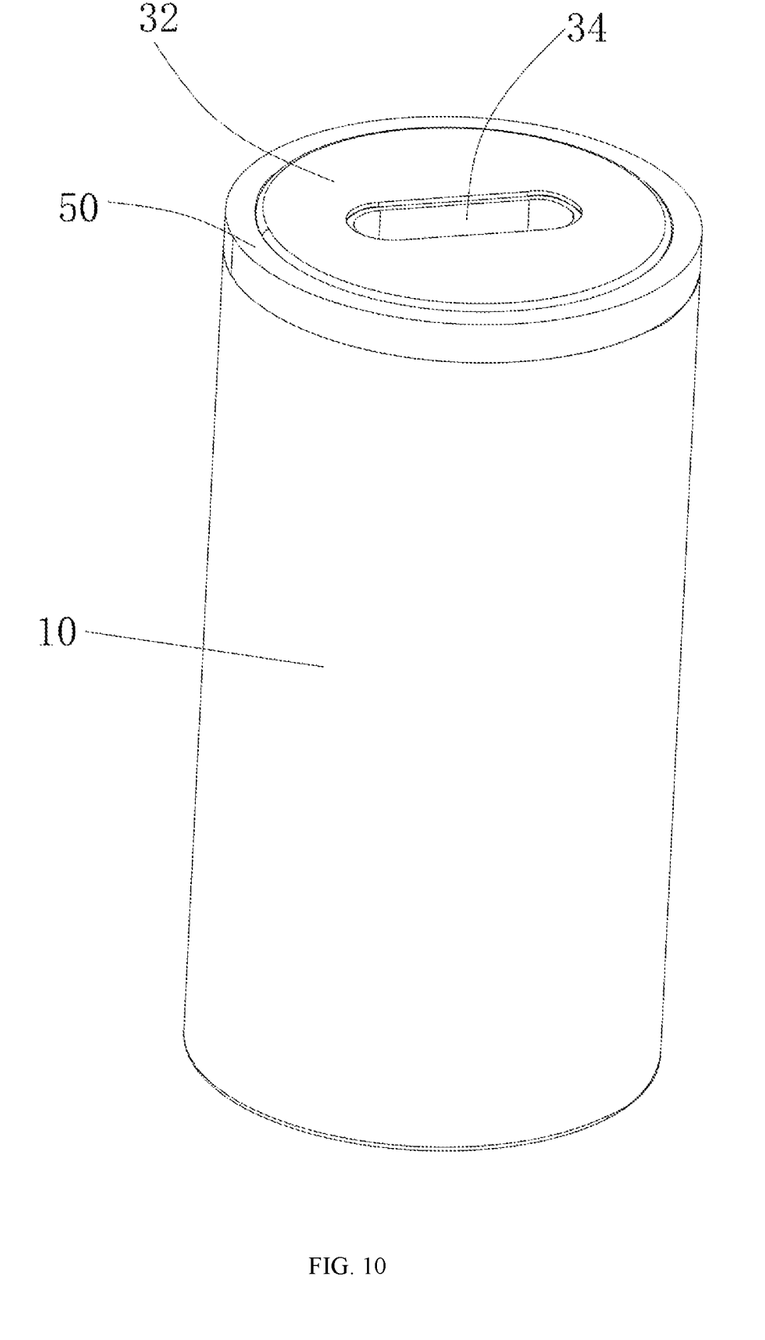
FIG. 10 is a three-dimensional view of a second embodiment of the invention.
Figure 11:
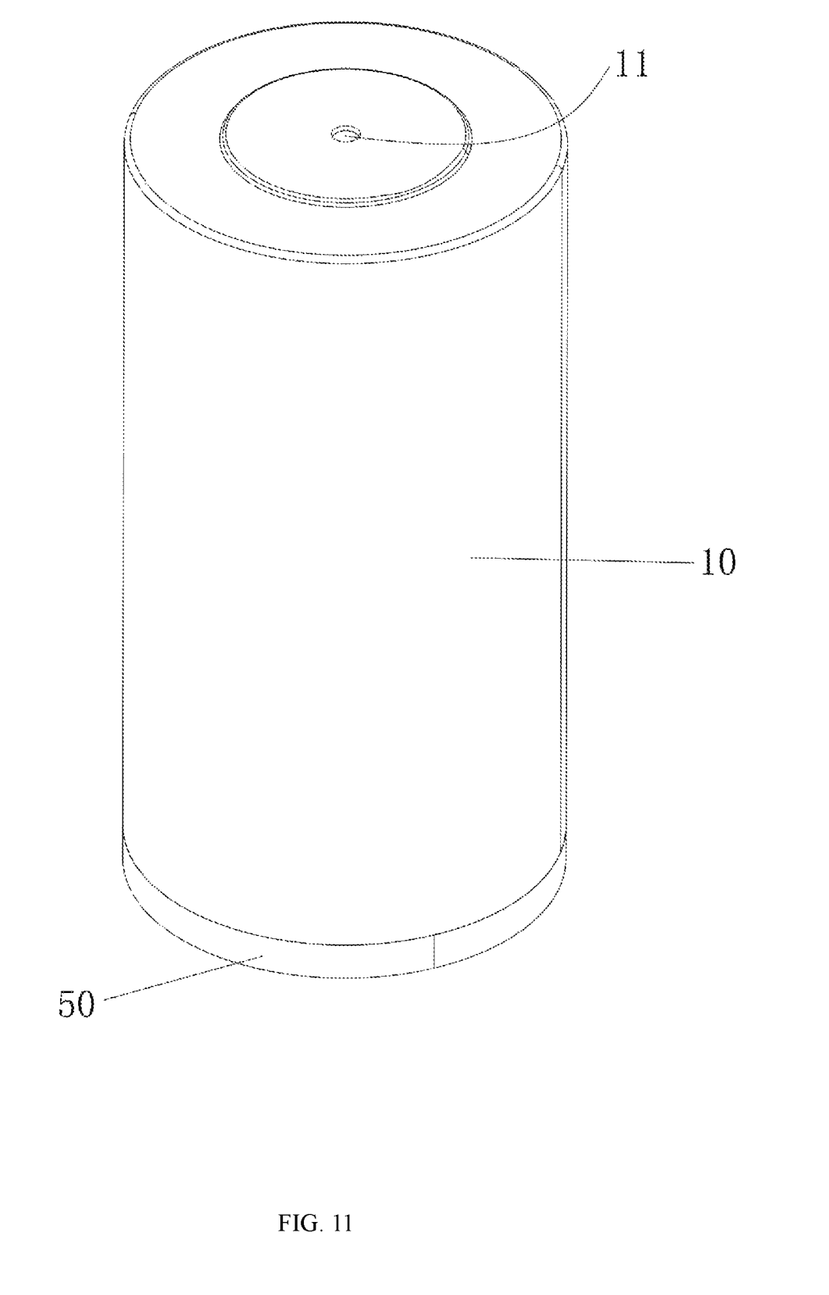
FIG. 11 is a three-dimensional view of the second embodiment of the invention, from another perspective.

Further referring FIG. 10 and FIG. 11 which are three-dimensional views of a second embodiment of the invention. The second embodiment is approximately identical with the first embodiment and differs from the first embodiment in the specification (for example, the height or the radius).

The key design of the invention is that the airflow sensor is arranged on the battery to control discharge of the cell, such that the battery can be used together with some atomizers to realize instant atomization when users inhale; and the integrated battery can respond quickly and can effectively avoid a waste of electric energy of the cell and atomizing liquid;

In addition, the integrated battery provided by the application has the advantage of high adaptability. The integrated battery is identical in overall shape and specification with other batteries on the market, and thus can be directly assembled together with other parts of atomizers, can be directly assembled on other products to be manufactured as a whole, and in subsequent production, can quickly respond to the demands in sales areas, thus having a broad market prospect.

The above embodiments are merely preferred ones of the invention, and are not intended to limit the technical scope of the invention. Any minor amendments, equivalent variations and modifications made to the above embodiments according to the technical essence of the invention should also fall within the scope of the technical solution of the invention.

What is claimed is:

1. An integrated battery using an airflow sensor for control, comprising an outer casing, a cell and a printed circuit board (PCBA), wherein the cell and the PCBA are both arranged in the outer casing, and the PCBA is electrically connected with the cell; the PCBA is provided with an airflow sensor; the outer casing is provided with an air inlet communicated with the airflow sensor; and when the airflow sensor senses an airflow change, the PCBA controls the cell to discharge;

wherein a sealing gasket and an insulating support are also arranged in the outer casing, the sealing gasket is arranged on an upper side of the cell, and the PCBA is arranged on an upper side of the sealing gasket;

the PCBA is also provided with a charging port, and the charging port penetrates through the insulating support and extends out of an upper surface of the outer casing; and an air inflow gap is reserved between the charging port and the insulating support, and the air inflow gap forms the air inlet.

2. The integrated battery using an airflow sensor for control according to claim 1, wherein the PCBA has a discharge terminal, and the discharge terminal comprises a positive plate and a negative plate arranged on the PCBA.

3. The integrated battery using an airflow sensor for control according to claim 1, wherein an air outlet is formed in a lower surface of the outer casing, and an air duct gap is reserved between the cell and an inner wall of the outer casing.

4. The integrated battery using an airflow sensor for control according to claim 1, wherein the sealing gasket is provided with an air hole corresponding to the airflow sensor.

5. The integrated battery using an airflow sensor for control according to claim 1, wherein the outer casing is made from an electrically conductive material, wherein the positive plate is electrically connected with the outer casing, and the negative plate is arranged on an upper surface of the insulating support.

6. The integrated battery using an airflow sensor for control according to claim 5, wherein the insulating support is provided with a mounting recess for mounting the negative plate, the negative plate is mounted on the mounting recess, and an insulating ring portion is arranged between an outer edge of the negative plate and an outer edge of the insulating support.

7. The integrated battery using an airflow sensor for control according to claim 1, wherein the airflow sensor is a Micro-electromechanical Systems (MEMS) microphone.

8. The integrated battery using an airflow sensor for control according to claim 1, wherein the PCBA is integrated with a battery protection chip and a main control chip, a positive pole of the cell is connected with a first resistor and is connected to the battery protection chip through the first resistor, a power output terminal of the battery protection chip is connected with the airflow sensor, an output terminal of the airflow sensor is connected with the main control chip, and an output terminal of the main control chip is connected with an output load and an indicator light.

\* \* \* \* \*